(12) United States Patent
Kim et al.

(10) Patent No.: US 10,927,237 B2
(45) Date of Patent: Feb. 23, 2021

(54) COMPOUND HAVING BIS PHENYLENE GROUP SUBSTITUTED WITH ALKYLAMIDE, COMPOSITION FOR CONTROLLING POLYPHENYLENE POLYMER FLOWABILITY AND METHOD OF POLYPHENYLENE POLYMER FLOWABILITY CONTROL USING THE SAME

(71) Applicant: KOREA RESEARCH INSTITUTE OF CHEMICAL TECHNOLOGY, Daejeon (KR)

(72) Inventors: Byoung Gak Kim, Daejeon (KR); Yong Seok Kim, Daejeon (KR); Young Jae Yoo, Daejeon (KR); Dong Gyun Kim, Suwon-si (KR); Seong Wook Lee, Daejeon (KR); Jun Woo Jeon, Daejeon (KR); Bo Mi Maeng, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 64 days.

(21) Appl. No.: 16/248,556

(22) Filed: Jan. 15, 2019

(65) Prior Publication Data
US 2019/0218368 A1 Jul. 18, 2019

(51) Int. Cl.
*C08K 5/375* (2006.01)
*C07C 323/41* (2006.01)
*C08G 75/0204* (2016.01)
*C08L 81/02* (2006.01)
*C08K 5/372* (2006.01)

(52) U.S. Cl.
CPC ............ *C08K 5/375* (2013.01); *C07C 323/41* (2013.01); *C08G 75/0204* (2013.01); *C08K 5/3725* (2013.01); *C08L 81/02* (2013.01)

(58) Field of Classification Search
CPC .... C08K 5/375; C07C 323/41; C08G 75/0204
USPC ........................................................ 524/225
See application file for complete search history.

(56) References Cited

U.S. PATENT DOCUMENTS 3,516,956 A * 6/1970 Reedy .................... C08L 67/02
524/220
2014/0087117 A1 3/2014 Duff et al.

FOREIGN PATENT DOCUMENTS

JP 03265642 A * 11/1991
JP 11-140315 A 5/1999

OTHER PUBLICATIONS

Daccord et al., Madromol. Chem., 184, 1869-1876, 1983. (Year: 1983).*
Elslager et al., Journal of Medicinal Chemistry, 12(3), 257-63, 1969. (Year: 1969).*
Dong et al., Electrochimica Acta, 55, 2275-2279, 2010. (Year: 2010).*
Abstract of JP 03-265642, Nov. 26, 1991. (Year: 1991).*
Lee et al. "Synthesis and Analysis of Flow Modifiers for PPS Flowability Enhancement" *Polymer(Korea)* 41(5):889-895 (2017).

* cited by examiner

*Primary Examiner* — Hui H Chin
(74) *Attorney, Agent, or Firm* — Klarquist Sparkman, LLP

(57) ABSTRACT

The present invention relates to a compound having a bis phenylene group substituted with alkylamide, a composition comprising the same for the control of polyphenylene polymer flowability and a method for controlling polyphenylene polymer flowability using the same. The said compound can improve the flowability of polyphenylene polymer so that it can be used for processing polyphenylene polymer to improve the flowability, thereby providing economic benefits by diversifying PPS parts and improving workability. In addition, the said compound can control and improve the flowability by regulating the length of phenyl-conjugated alkyl, so that it can be effectively used as a flowability regulator of polyphenylene polymer particularly polyphenylene sulfide.

8 Claims, 11 Drawing Sheets

COMPOUND HAVING BIS PHENYLENE GROUP SUBSTITUTED WITH ALKYLAMIDE, COMPOSITION FOR CONTROLLING POLYPHENYLENE POLYMER FLOWABILITY AND METHOD OF POLYPHENYLENE POLYMER FLOWABILITY CONTROL USING THE SAME

CROSS REFERENCE TO RELATED APPLICATION

This patent application claims the benefit of priority under 35 U.S.C. § 119 from Korean Patent Application No. 10-2018-0005136, filed Jan. 15, 2018, the contents of which are incorporated herein by reference.

BACKGROUND OF THE INVENTION

1. Field of the Invention

The present invention relates to a compound having a bis phenylene group substituted with alkylamide, a composition comprising the same for the control of polyphenylene polymer flowability and a method for controlling polyphenylene polymer flowability using the same.

2. Description of the Related Art

Polyphenylene sulfide (PPS) is a high performance thermoplastic engineering plastic developed by Philips Petroleum, USA. PPS has the glass transition temperature of 80-90° C. and the melting point thereof is approximately 280° C.

Particularly, polyphenylene sulfide is classified into a super engineering plastic and displays excellent chemical resistance, thermal stability, self-flame resistance and excellent mechanical properties. PPS is lighter than other engineering plastics and has superior physical properties, so that it has been applied as an alternative material for metals in various industrial fields. However, due to the low processing efficiency of PPS resulted from its low flowability and high processing temperature in the course of injection molding, the use of PPS in various fields is limited.

In general, PPS is produced as a composite material with glass fiber added to enhance the mechanical properties, which is another factor that hinders the processing efficiency. Therefore, it is necessary to increase the processing efficiency of PPS in order to use PPS in various fields.

Generally, a polymer blend, a copolymer preparation and an additive are widely used to increase the processing efficiency of a polymer. Firstly, in the polymer blend method, a lot of blends of PPS and other polymers have been studied, the method is not efficient in controlling the physical properties of PPS because the miscibility between them is poor or almost none. Secondly, in the case of the copolymer preparation, the method has an advantage of easy workability, but has difficulty in polymer synthesis and risk of the changes of physical properties of the conventional polymer. Lastly, the method of using an additional lubricant has an advantage of controlling the process temperature with a small amount of an additive. A representative example is nylon, which is widely used as a material for automobile bumpers, whose processing efficiency was significantly increased by using an additive and thus this method is now widely used in industrial fields.

PATENT REFERENCE (Patent Reference 1) US Patent No. US20140087117 A1

SUMMARY OF THE INVENTION

It is an object of the present invention to provide a composition comprising a bis phenylene group substituted with alkylamide for controlling the polyphenylene polymer flowability.

It is another object of the present invention to provide a polyphenylene polymer composition with controlled flowability.

It is further an object of the present invention to provide a method for controlling the flowability of the polyphenylene polymer composition.

It is also an object of the present invention to provide a compound having a bis phenylene group substituted with alkylamide.

To achieve the above objects, the present invention provides a composition comprising the compound represented by formula 1 below for controlling the polyphenylene polymer flowability:

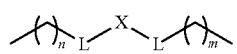

[Formula 1]

(In formula 1,
n and m are each independently an integer of 5 to 30;
L is C(=O)NH or NHC(=O); and
X is

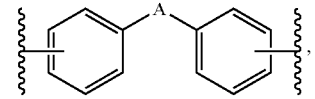

at this time A is S, O, C(=O), $SO_4$, $SO_2$, $CR^2R^3$ or $NR^4$, wherein $R^2$, $R^3$ and $R^4$ are independently hydrogen, straight or branched $C_{1-5}$ alkyl or nonsubstituted $C_{6-10}$ aryl.).

According to another aspect of the present invention, the present invention provides a polyphenylene polymer composition with controlled flowability comprising the polyphenylene polymer and the flowability controlling composition, wherein the flowability controlling composition is contained at the concentration of 0.01-10 weight part by 100 weight part of the polyphenylene polymer.

According to another aspect of the present invention, the present invention provides a method for controlling the flowability of a polyphenylene polymer composition comprising the steps of adding the flowability controlling composition above at the concentration of 0.01-10 weight part to 100 weight part of the polyphenylene polymer and melt-mixing thereof.

According to another aspect of the present invention, the present invention provides a compound represented by formula 1 below:

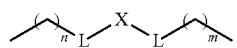

[Formula 1]

(In formula 1,
n and m are each independently an integer of 5 to 30;
L is C(=O)NH or NHC(=O); and
X is

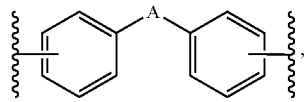

at this time A is S, O, C(=O), SO$_4$, SO$_2$, CR$^2$R$^3$ or NR$^4$, wherein R$^2$, R$^3$ and R$^4$ are independently hydrogen, straight or branched C$_{1-5}$ alkyl or nonsubstituted C$_{6-10}$ aryl.).

Advantageous Effect

The compound having a bis phenylene group substituted with alkylamide represented by formula 1 of the present invention can improve the flowability of polyphenylene polymer so that it can be used for processing polyphenylene polymer to improve the flowability, thereby providing economic benefits by diversifying PPS parts and improving workability. In addition, the said compound can control and improve the flowability by regulating the length of phenyl-conjugated alkyl, so that it can be effectively used as a flowability regulator of polyphenylene polymer particularly polyphenylene sulfide.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Hereinafter, the present invention is described in detail.

According to an aspect of the present invention, the present invention provides a composition comprising a compound having a bis phenylene group substituted with alkylamide for controlling polyphenylene polymer flowability, more precisely a composition comprising the compound represented by formula 1 below for controlling polyphenylene polymer flowability.

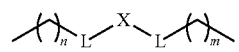

[Formula 1]

(In formula 1,
n and m are each independently an integer of 5 to 30;
L is C(=O)NH or NHC(=O); and
X is

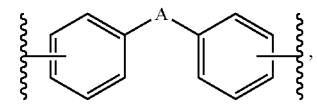

at this time A is S, O, C(=O), SO$_4$, SO$_2$, CR$^2$R$^3$ or NR$^4$, wherein R$^2$, R$^3$ and R$^4$ are independently hydrogen, straight or branched C$_{1-5}$ alkyl or nonsubstituted C$_{6-10}$ aryl.).

In formula 1 above, n and m are each independently an integer of 5 to 25.

Also, n and m are each independently an integer of 8 to 25.

Also, n and m are each independently an integer of 8 to 17.

Also, n and m are each independently an integer of 8 to 12.

Also, n and m are each independently an integer of 8 or 12.

Figure 6:
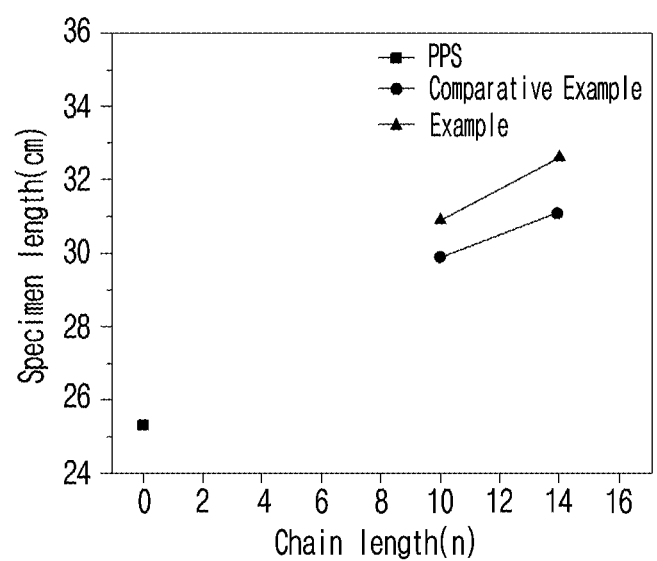
FIG. 6 is a graph illustrating the comparison of the specimen length of the polyphenylene sulfide mixed with the compound of an example of the present invention and the polyphenylene sulfide mixed with the compound of a comparative example of the present invention.
Figure 7:
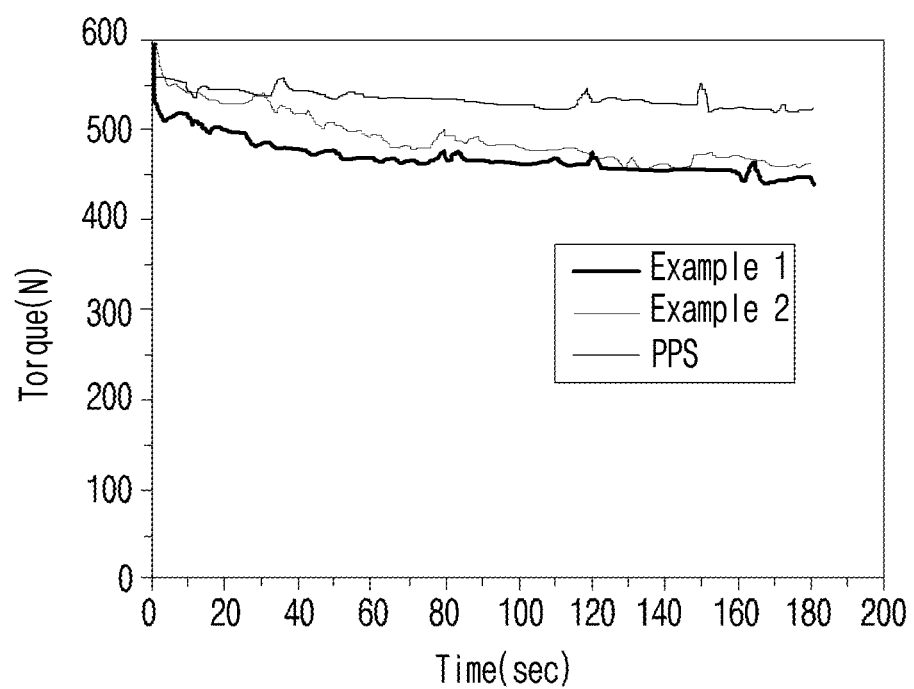
FIG. 7 is a graph illustrating the torque of the polyphenylene sulfide mold mixed with the flowability controlling composition of the present invention.
Figure 8:
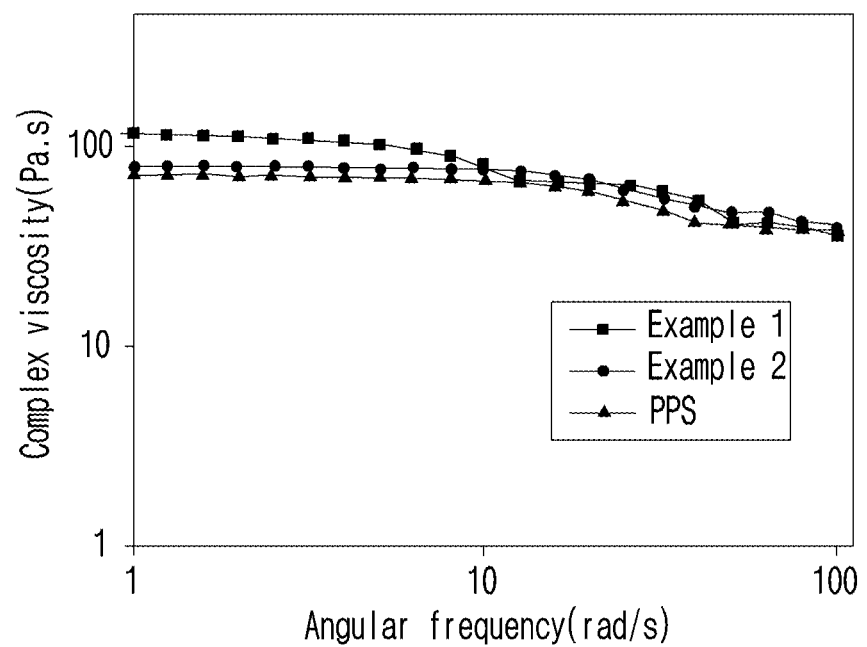
FIG. 8 is a graph illustrating the viscosity of the polyphenylene sulfide mold mixed with the flowability controlling composition of the present invention.

At this time, the length of n and m affects the improvement of polyphenylene polymer flowability by the flowability controlling composition (see Experimental Example A and FIGS. 6 to 8). Thus, the improvement of flowability can be controlled by regulating the length of alkyl.

The compound represented by formula 1 exhibits a significantly excellent flowability improving effect, compared with other linkers particularly ether linkers such as —O—, due to the link of alkyl to phenylene through an amide bond (see Experimental Example A and FIG. 6).

In formula 1 above,

A is S, O, SO$_2$ or CR$^2$R$^3$, wherein, R$^2$ and R$^3$ are independently hydrogen, straight or branched C$_{1-3}$ alkyl or nonsubstituted phenyl.

Also, A is S, O or SO$_2$.

Also, A is S or SO$_2$.

Also, A is S.

Specific examples of the compound represented by formula 1 above are the following compounds.

(1) N,N'-(4,4'-thiobis(4,1-phenylene))bis(decanamide);

(2) N,N'-(4,4'-thiobis(4,1-phenylene))ditetradecanamide.

The flowability controlling composition above can be used to improve the flowability in the course of injection molding or in the process of polyphenylene polymer particularly polyphenylene sulfide and can be prepared in various forms such as liquid and solid, etc. In the following experimental examples, the flowability controlling composition was prepared in powder form, but not always limited thereto.

The preferable concentration of the flowability controlling composition is 0.01-10 weight part by 100 weight part of polyphenylene polymer, more preferably 0.1-5 weight part and most preferably 0.3-3 weight part by 100 weight part of polyphenylene polymer. In the following experimental examples, the concentration of the flowability controlling composition was 1 weight part (parts per hundred rubber, phr), but not always limited thereto. The concentration can be properly adjusted according to the kind of a polymer to regulate the improvement level of flowability.

The thermal stability of the compound represented by formula 1 was evaluated. As a result, the compound was stable at least for 20 minutes at 320° C., suggesting that the compound can be useful as a flowability controlling composition with playing a role as an additive because the compound is not decomposed at a process temperature of polyphenylene polymer such as polyphenylene sulfide (see Experimental Example 1 and FIGS. 4 and 5).

The flowability control effect of the flowability controlling composition above was evaluated. As a result, it was confirmed that the specimen length was significantly increased, the torque value was remarkably decreased, and the viscosity was also remarkably decreased, compared with when the specimen was prepared without being added with the flowability controlling composition of the invention (see Experimental Example A and FIGS. 6 to 8).

The compound having a bis phenylene group substituted with alkylamide represented by formula 1 can improve the flowability of polyphenylene polymer so that it can be used for processing polyphenylene polymer to improve the flowability, thereby providing economic benefits by diversifying PPS parts and improving workability. In addition, the said compound can control and improve the flowability by regulating the length of phenyl-conjugated alkyl, so that it can be effectively used as a flowability regulator of polyphenylene polymer particularly polyphenylene sulfide.

According to another aspect of the present invention, the present invention provides a polyphenylene polymer composition comprising the polyphenylene polymer and the flowability controlling composition wherein the polyphenylene polymer flowability was regulated, and the flowability controlling composition was used at the concentration of 0.01 to 10 weight part by 100 weight part of the polyphenylene polymer.

In the polyphenylene polymer composition with controlled flowability, the flowability controlling composition was preferably included at the concentration of 0.01-10 weight part, more preferably at the concentration of 0.1-5 weight part, and most preferably 0.3-3 weight part by 100 weight part of the polyphenylene polymer to regulate the flowability. In the following experimental examples, the concentration of the flowability controlling composition was 1 weight part (parts per hundred rubber, phr), but not always limited thereto. The concentration can be properly adjusted according to the kind of a polymer to regulate the improvement level of flowability.

According to another aspect of the present invention, the present invention provides a method for controlling the flowability of a polyphenylene polymer composition comprising the steps of adding the flowability controlling composition above at the concentration of 0.01-10 weight part to 100 weight part of the polyphenylene polymer and melt-mixing thereof.

In the flowability controlling method above, the flowability controlling composition can be used at the concentration of 0.1-5 weight part and preferably 0.3-3 weight part by 100 weight part of polyphenylene polymer. In the following experimental examples, the concentration of the flowability controlling composition was 1 weight part (parts per hundred rubber, phr), but not always limited thereto. The concentration can be properly adjusted according to the kind of a polymer to regulate the improvement level of flowability.

A machine used for melt mixing is not particularly limited and any machine that can be used for melt mixing of polymer, which is accepted by those in the art, can be used. In examples of the present invention, a microcompounder was used. Particularly, melt mixing can be performed at a temperature higher than the melting point of the polymer by 20° C.~40° C. after the polyphenylene polymer and the flowability controlling composition are added to the machine and then heated. In an example of the present invention, polyphenylene sulfide was used as a polymer and the reaction was induced at 300° C.~320° C., the temperature 20° C.~40° C. higher than the melting point of polyphenylene sulfide (approximately 280° C.). The reaction can be performed at different temperatures according to the kind of the polymer.

At this time, if the reaction is not induced at a temperature higher than 20° C. above the melting point of the polymer, there would be a problem in the extrusion of the polymer. If the reaction is induced at a temperature higher than 40° C. than the melting point, a drop phenomenon would occur. Therefore, the preferable temperature for the reaction is 20° C.~40° C. higher than the melting point of the polymer. The melt mixing time is not particularly limited, but can be performed for 3 minutes.

According to another aspect of the present invention, the present invention provides a compound represented by formula 1.

[Formula 1]

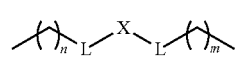

(In formula 1,
n and m are each independently an integer of 5 to 30;
L is C(=O)NH or NHC(=O); and
X is

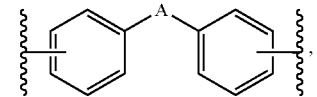

at this time A is S, O, C(=O), $SO_4$, $SO_2$, $CR^2R^3$ or $NR^4$, wherein $R^2$, $R^3$ and $R^4$ are independently hydrogen, straight or branched $C_{1-5}$ alkyl or nonsubstituted $C_{6-10}$ aryl.).

In formula 1 above,
n and m are each independently an integer of 5 to 25.
Also, n and m are each independently an integer of 8 to 25.
Also, n and m are each independently an integer of 8 to 17.
Also, n and m are each independently an integer of 8 to 12.
Also, n and m are each independently an integer of 8 or 12.

At this time, the length of n and m affects the improvement of polyphenylene polymer flowability by the flowability controlling composition (see Experimental Example A and FIGS. 6 to 8). Thus, the improvement of flowability can be controlled by regulating the length of alkyl.

The compound represented by formula 1 exhibits a significantly excellent flowability improving effect, compared with other linkers particularly ether linkers such as —O—, due to the link of alkyl to phenylene through an amide bond (see Experimental Example A and FIG. 6).

In formula 1 above,

A is S, O, SO$_2$ or CR$^2$R$^3$, wherein, R$^2$ and R$^3$ are independently hydrogen, straight or branched C$_{1-3}$ alkyl or nonsubstituted phenyl.

Also, A is S, O or SO$_2$.

Also, A is S or SO$_2$.

Also, A is S.

Specific examples of the compound represented by formula 1 above are the following compounds.

(1) N,N'-(4,4'-thiobis(4,1-phenylene))bis(decanamide);

(2) N,N'-(4,4'-thiobis(4,1-phenylene))ditetradecanamide.

Practical and presently preferred embodiments of the present invention are illustrative as shown in the following Examples.

However, it will be appreciated that those skilled in the art, on consideration of this disclosure, may make modifications and improvements within the spirit and scope of the present invention.

<Example 1> Preparation of N,N'-(4,4'-thiobis(4,1-phenylene))bis(decanamide)

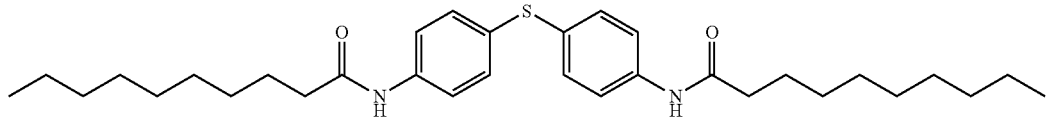 [SMILES: CCCCCCCCCC(=O)Nc1ccc(Sc2ccc(NC(=O)CCCCCCCCC)cc2)cc1]

Moisture in a 250 ml two-neck round flask was eliminated, to which 30 mmol bis (4-aminophenylsulfide), 60 mmol decanoic acid, 1.32 g of calcium chloride, 18.57 ml of triphenylphosphite, 3 ml of pyridine and 22 ml of NMP were added, followed by reaction at 60° C. for 1 hour, at 90° C. for 2 hours and at 120° C. for 8 hours with refluxing. Upon completion of reaction, the reaction mixture was precipitated in methanol. The precipitate was filtered in vacuo and then precipitated again in hot methanol to give a target product. The obtained product was vacuum dried. As a result, N,N'-(4,4'-thiobis(4,1-phenylene))bis(decanamide) powder with white color was obtained (yield: 85%).

<Example 2> Preparation of N,N'-(4,4'-thiobis(4,1-phenylene))ditetradecanamide

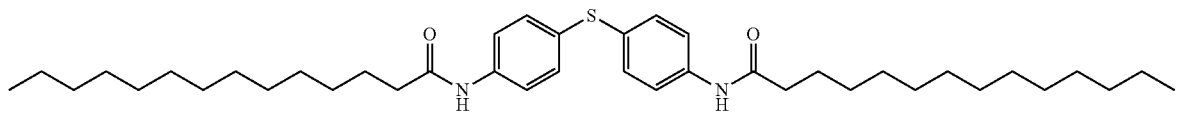 [SMILES: CCCCCCCCCCCCCC(=O)Nc1ccc(Sc2ccc(NC(=O)CCCCCCCCCCCCC)cc2)cc1]

N,N'-(4,4'-thiobis(4,1-phenylene))ditetradecanamide was prepared by the same manner as described in Example 1 except that myristic acid was used instead of decanoic acid.

To investigate the difference of the alkyl bound to the thiobisphenylene compound, the compounds of Comparative Examples 1~2 which had —O— linker and the same alkyl length were synthesized.

<Comparative Example 1> Preparation of bis(4-(decyloxy)phenyl)sulfane

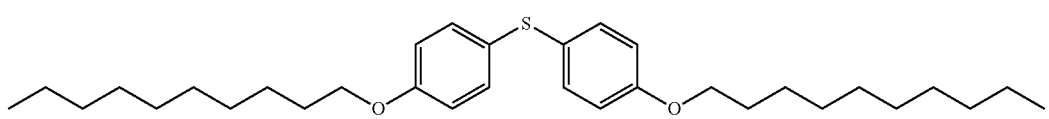 [SMILES: CCCCCCCCCCOc1ccc(Sc2ccc(OCCCCCCCCCC)cc2)cc1]

Thiodiphenol (4.37 g, 0.02 mol) and potassium carbonate (6.91 g, 0.06 mol) were dissolved in 100 mL of DMF in a 250 mL three-neck flask, followed by stirring at 80° C. for 30 minutes. 1-Bromodecane (0.05 mol) was added thereto, followed by stirring for 12 hours for further reaction. Upon completion of the reaction, the reaction mixture was precipitated in methanol. The precipitate was filtered in vacuo and then precipitated again in hot methanol to give a target product. The obtained product was vacuum dried. As a result, bis(4-(decyloxy)phenyl)sulfane powder was obtained.

<Comparative Example 2> Preparation of bis(4-(tetradecyloxy)phenyl)sulfane

TABLE 1

|  | Calculated Value | | | | | Measured Value | | | | |
| --- | --- | --- | --- | --- | --- | --- | --- | --- | --- | --- |
|  | C (%) | H (%) | O (%) | S (%) | N (%) | C (%) | H (%) | O (%) | S (%) | N (%) |
| Comparative Example | | | | | | | | | | |
| 1 | 77.1 | 10.1 | 6.4 | 6.4 | — | 77.2 | 10.2 | 6.5 | 6.1 | — |
| 2 | 78.6 | 10.9 | 5.2 | 5.3 | — | 78.7 | 11.0 | 5.3 | 5.0 | — |
| Example | | | | | | | | | | |
| 1 | 73.2 | 9.2 | 6.1 | 6.1 | 5.3 | 73.5 | 8.3 | 7.0 | 5.9 | 5.4 |
| 2 | 75.4 | 10.1 | 5.0 | 5.0 | 4.4 | 75.7 | 10.2 | 4.6 | 5.1 | 4.4 |

Figure 2:
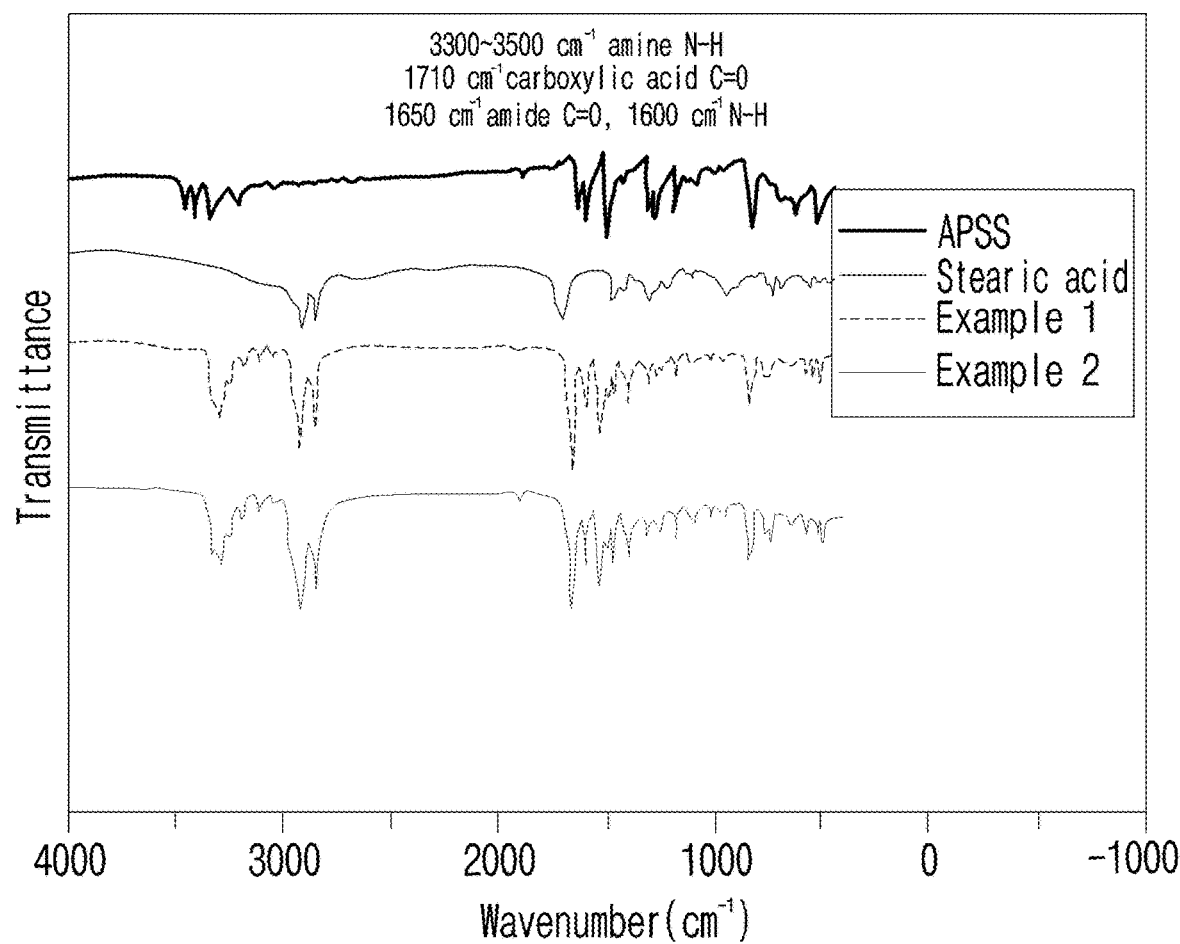
FIG. 2 is a graph illustrating the results of FTIR spectrum analysis with the compounds of examples of the present invention.

FIG. 2 presents the results of FTIR spectrum analysis with the compounds of examples of the present invention.

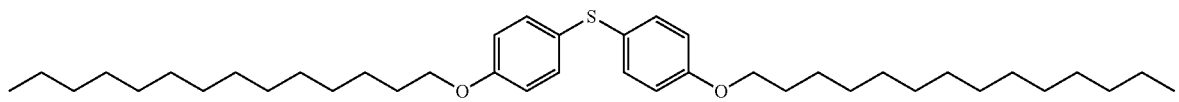 [SMILES: CCCCCCCCCCCCCCOc1ccc(Sc2ccc(OCCCCCCCCCCCCCC)cc2)cc1]

Bis(4-(tetradecyloxy)phenyl)sulfane was prepared by the same manner as described in Comparative Example 1 except that 1-bromotetradecane was used instead of 1-bromodecane.

<Experimental Example 1> Compound Analysis

Figure 1:
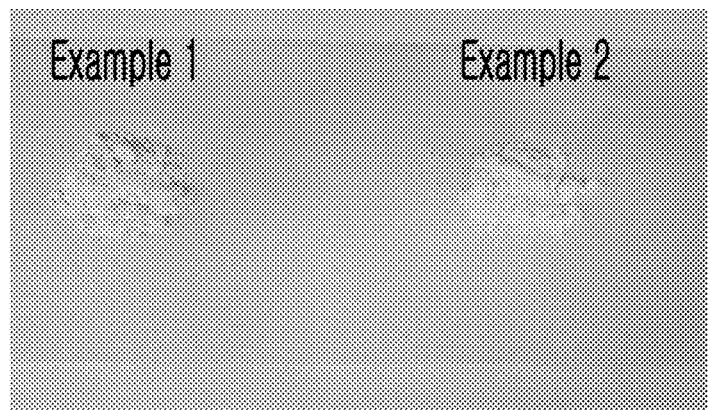
FIG. 1 is a set of photograph images illustrating the compounds of examples of the present invention.

The following experiments were performed to investigate the production, melting point, impurities and thermal stability of the compounds prepared in examples and comparative examples. FIG. 1 presents the images of the compounds prepared in examples of the present invention.

1-1. Confirmation of Compound Production

The compounds of examples were analyzed by using (bis(4-amino phenylsulfide, APSS in FIG. 2), stearic acid and FTIR (A2 technologies Exoscan). At this time, aliphatic acid was only to observe COOH peak, so stearic acid alone was measured as a comparative group.

The structures of the compounds of comparative examples were analyzed by $^1$H NMR (Bruker AMX-300 MHz spectrometer).

Elemental analysis (EA, Flash 2000 organic elemental analyzer) was used to confirm that the compounds of examples and comparative examples were well synthesized.

Figure 9:
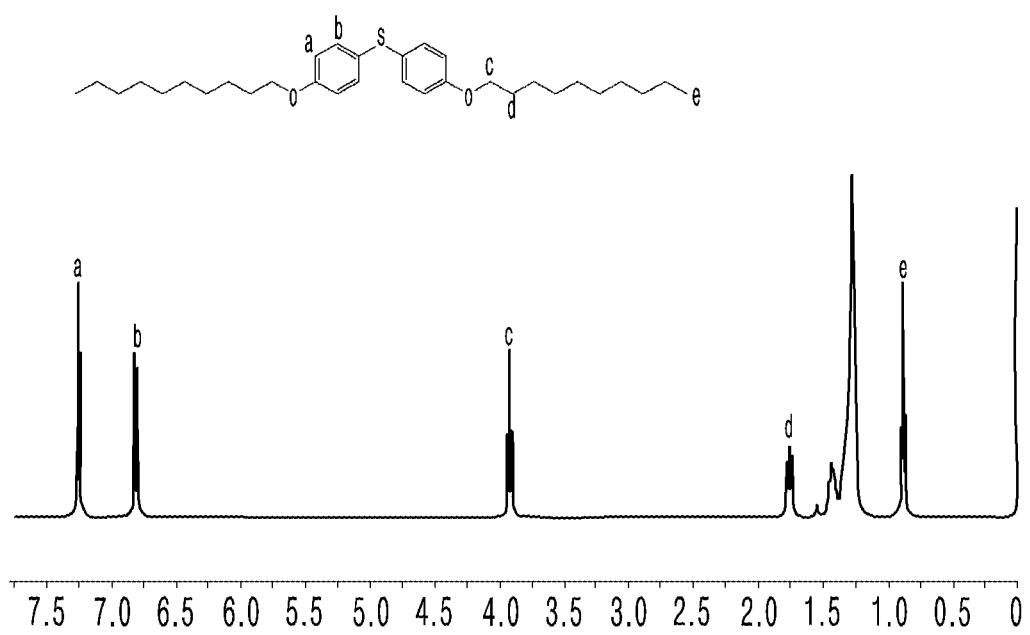
FIG. 9 and FIG. 10 present the results of $^1$H-NMR with the compounds of comparative examples of the present invention.
Figure 10:
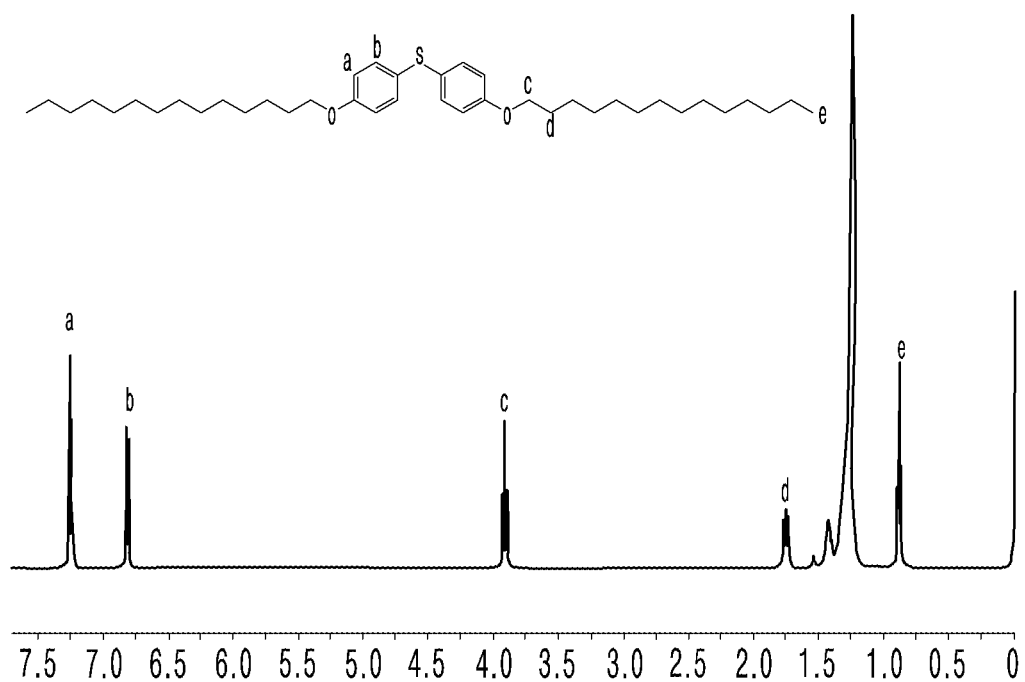

The results of FTIR spectrum analysis of the compounds of examples are shown in FIG. 2, the results of $^1$H NMR analysis of the compounds of comparative examples are shown in FIGS. 9 and 10, and the results of EA analysis of the compounds of examples and comparative examples are shown in Table 1 below.

FIG. 9 and FIG. 10 present the results of $^1$H-NMR with the compounds of comparative examples of the present invention.

As shown in FIG. 2, the stretching vibration of —NH2, which is the characteristic peak of aminophenyl sulfide (APSS), was confirmed near 3300 cm$^{-1}$. The stretching vibration of —COOH C═O, which is the characteristic peak of stearic acid, was confirmed near 1710 cm$^{-1}$. From the data obtained after the synthesis of the compounds of examples above, the stretching vibration of C═O was confirmed at 1650 cm$^{-1}$, the characteristic peak of amide, and the bending vibration of N—H was confirmed at 1600 cm$^{-1}$, suggesting that the amide bond was generated and thus the compounds were successfully synthesized. As shown in Table 1, from the results of EA analysis, it was confirmed that the compounds of examples were successfully synthesized by observing that the theoretical values (calculated values) were in accord with the experimental values (measured values) without big differences.

As shown in FIGS. 9 and 10, it was confirmed that the compounds of comparative examples were successfully synthesized by observing the proper corresponding NMR peaks. As shown in Table 1, from the results of EA analysis, it was also confirmed that the compounds of comparative examples were successfully synthesized by observing that the theoretical values (calculated values) were in accord with the experimental values (measured values) without big differences.

1-2. Confirmation of Melting Point

The melting points of the compounds of examples of the present invention were measured by differential scanning calorimetry (DSC, TA Instrument). The results are shown in FIG. 3.

Figure 3:
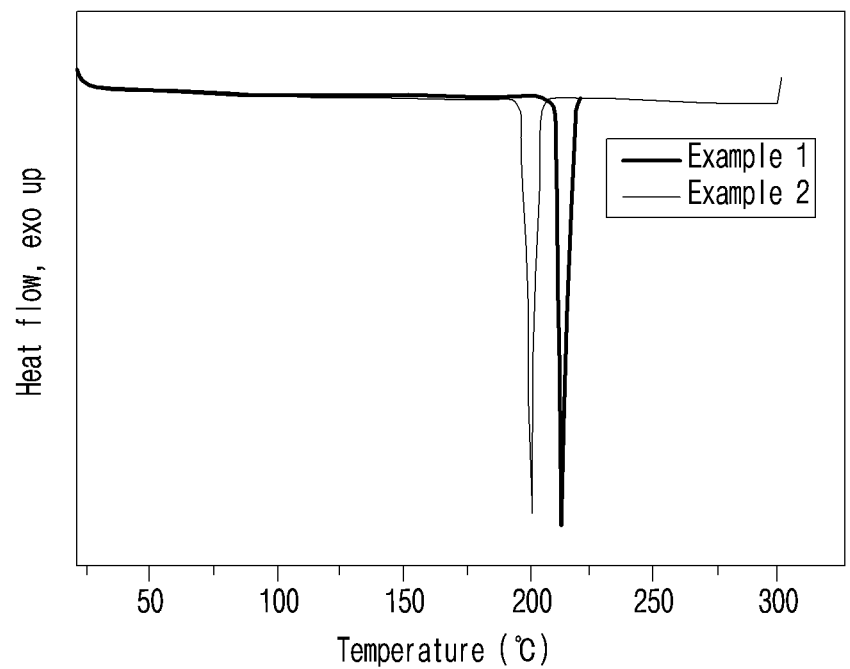
FIG. 3 is a graph illustrating the melting points of the compounds of examples of the present invention.

FIG. 3 is a graph illustrating the melting points of the compounds of examples of the present invention.

As shown in FIG. 3, the melting points of the compounds of examples of the present invention were lowered to 210° C. and 200° C., respectively. The decrease of the melting point can be explained by the fact that the N—H hydrogen bond of amide becomes weaker as the length of alkyl chain is longer in amide compounds.

1-3. Confirmation of Thermal Stability

Figure 4:
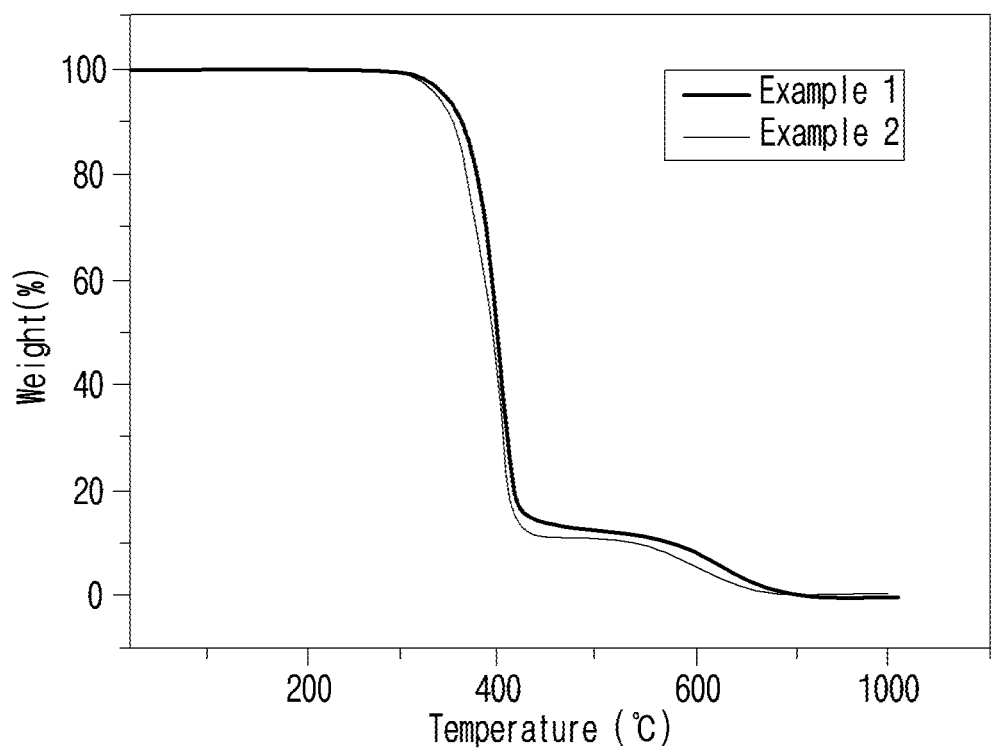
FIG. 4 is a graph illustrating the results of thermogravimetric analysis with the compounds of examples of the present invention.

To investigate the thermal stability of the compounds of examples of the present invention, thermogravimetric analysis (TGA, TA Instrument) was performed with raising temperature from room temperature to 800° C. at the heating rate of 10° C./min in a nitrogen atmosphere. The results are shown in FIG. 4. Isothermal test was also performed at 320° C. for 60 minutes. The results are shown in FIG. 5.

FIG. 4 is a graph illustrating the results of thermogravimetric analysis with the compounds of examples of the present invention.

Figure 5:
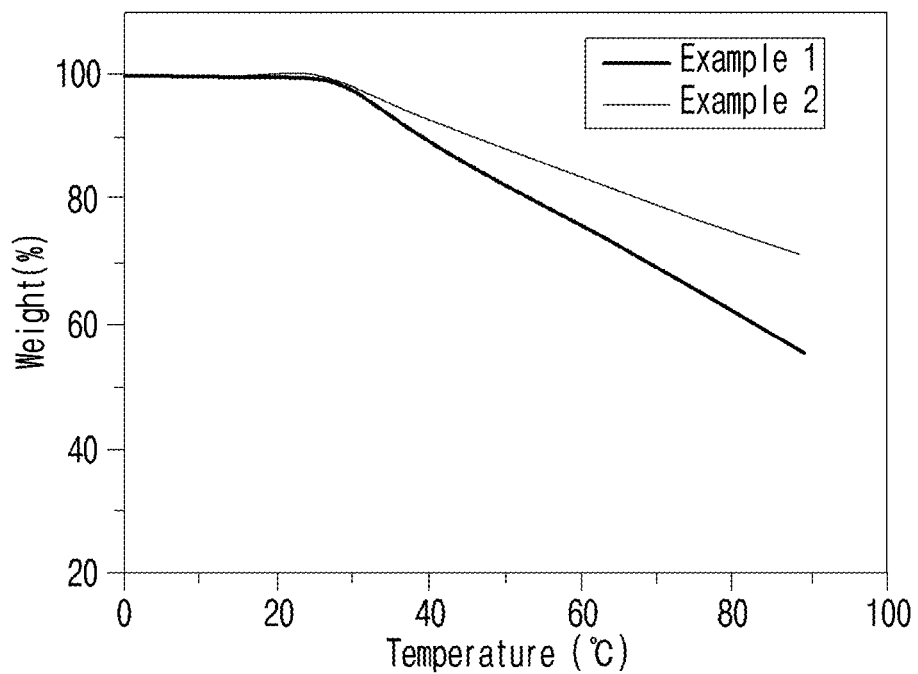
FIG. 5 is a graph illustrating the results of isothermal test with the compounds of examples of the present invention.

FIG. 5 is a graph illustrating the results of isothermal test with the compounds of examples of the present invention.

As shown in FIG. 4, it was confirmed by TGA analysis that the compounds of examples of the present invention had the thermal stability at the temperature of 300° C. or higher.

As shown in FIG. 5, it was confirmed by isothermal test that the compounds of examples of the present invention were stable at least for 20 minutes at 320° C. Therefore, the compounds of examples of the present invention above can be useful as a flowability controlling composition because it is not decomposed at a processing temperature of polyphenylene polymer such as polyphenylene sulfide.

<Example A> Preparation of Polyphenylene Polymer Specimen Using the Flowability Controlling Composition Comprising the Example Compound Specimens were prepared as follows in order to evaluate the effect of the polyphenylene polymer flowability controlling composition comprising the compounds of examples of the present invention. At this time, polyphenylene sulfide was used as the polyphenylene polymer. To compare the flowability controlling effect according to the types of alkyl linker, specimens were prepared by using the compounds of comparative examples of the present invention as well.

Specimen Preparation

The example compound and the comparative example compound were added (1 phr, parts per hundred rubber) respectively to 14.85 g of polyphenylene sulfide, followed by melt-mixing at 320° C. for 3 minutes in a microcompounder (Xplore, Twin-screw 15 mL). The prepared mixture was injected into a mold set at the temperature of 80° C. By which, spiral specimen was prepared for the investigation of flowability and disc specimen was prepared for the measurement of viscosity.

Figure 11:
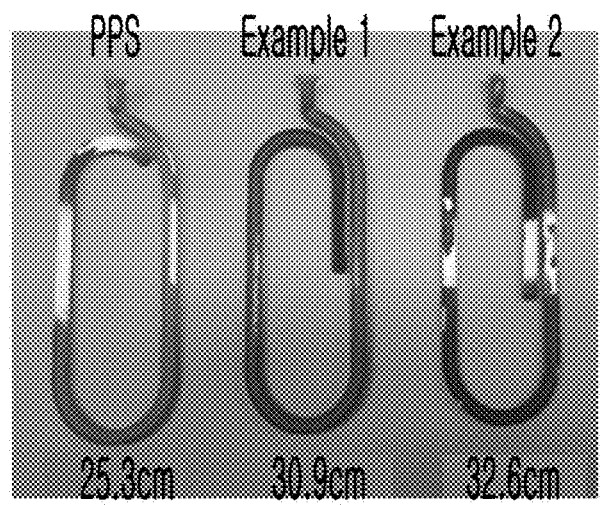
FIG. 11 is a set of photograph images illustrating the polyphenylene sulfide samples mixed with the compounds of examples of the present invention.

<Experimental Example A> Evaluation of Polyphenylene Sulfide Flowability Controlling Effect of the Flowability Controlling Composition Containing the Example Compound 1. Evaluation of Flowability Controlling Effect by Measuring the Specimen Length The polyphenylene sulfide flowability controlling effect of the flowability controlling composition was evaluated by measuring the length of specimen prepared in Example A. The images of the specimen prepared by mixing the example compound are shown in FIG. 11.

FIG. 6 is a graph illustrating the comparison of the specimen length of the polyphenylene sulfide mixed with the compound of an example of the present invention and the polyphenylene sulfide mixed with the compound of a comparative example of the present invention.

As shown in FIG. 6, the specimen length was significantly increased when the flowability controlling composition comprising the example compound was added, compared with the polyphenylene sulfide (PPS) specimen prepared without adding any flowability regulators. Particularly, when the amide based flowability controlling composition like the compounds of examples of the present invention was added, the specimen length was significantly increased, compared when the ether based flowability controlling composition like the compounds of comparative examples of the present invention was added. Therefore, it was confirmed that the flowability controlling composition comprising the example compound was able to increase the flowability of polyphenylene sulfide significantly.

Overall, as the length of alkyl chain of the flowability regulator was increased, the length of the spiral specimen was also increased.

2. Measurement of Torque

Torque was measured by using a v1.5 program linked to the microcompounder. Particularly, the example compound was added (0.1~3 phr) to 14.85 g of polyphenylene sulfide, followed by melt-mixing at 320° C. for 3 minutes in a microcompounder. The prepared mixture was injected into a mold set at the temperature of 80° C. The torque changes during the melt-mixing were measured by using v.1.5 microcompounder program. The results are shown in FIG. 7.

FIG. 7 is a graph illustrating the torque of the polyphenylene sulfide mold mixed with the flowability controlling composition of the present invention.

As shown in FIG. 7, the torques of the compounds of examples of the present invention were all reduced, suggesting that the friction generated during the polyphenylene sulfide processing and the pressure applied to the screw during the extrusion were reduced by decreasing the torque.

Even though it was not significant, the torque was reduced as the alkyl chain became longer in the flowability controlling composition comprising the example compound. This is because, as the alkyl group shows hydrophobicity, the longer the length, the better the miscibility with the polymer matrix and the lower the torque.

3. Measurement of Viscosity

Viscosity was measured at 320° C. by using a rotational rheometer (ARES-02, TA Instrument). Particularly, to measure the viscosity, specimens were prepared by using a disc mold prepared in Example A and then viscosity was measured at 320° C. which was the processing temperature of PPS. The results are shown in FIG. 8.

FIG. 8 is a graph illustrating the viscosity of the polyphenylene sulfide mold mixed with the flowability controlling composition of the present invention.

As shown in FIG. 8, it was confirmed that the viscosity of PPS was reduced by the addition of the flowability controlling composition comprising the compound of the present invention.

From the results of the example and experimental example above, it was confirmed that the flowability controlling composition comprising the compound represented by formula 1 of the present invention was useful to improve the flowability of polyphenylene polymer such as PPS (polyphenylene sulfide) in the course of processing polyphenylene polymer and was thereby confirmed to provide economic benefits by diversifying PPS parts and improving workability.

The compound represented by formula 1 can control the flowability depends on the length of alkyl, indicating that the compound can improve the flowability by regulating the length of alkyl.

The compound having a bis phenylene group substituted with alkylamide, represented by formula 1, can improve the flowability of polyphenylene polymer so that it can be used for processing polyphenylene polymer to improve the flowability, thereby providing economic benefits by diversifying PPS parts and improving workability. In addition, the said compound can control and improve the flowability by regulating the length of phenyl-conjugated alkyl, so that it can be effectively used as a flowability regulator of polyphenylene polymer particularly polyphenylene sulfide.

What is claimed is:

1. A polyphenylene polymer composition with controlled flowability, comprising:
   a polyphenylene polymer; and
   a flowability controlling composition for controlling the polyphenylene polymer flowability, comprising a compound represented by Formula 1, wherein the flowability controlling composition is contained at the concentration of 0.01-10 weight part by 100 weight part of the polyphenylene polymer;

[Formula 1]

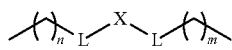

wherein,
n and m are each independently an integer of 5 to 30;
L is C(=O)NH or NHC(=O); and
X is

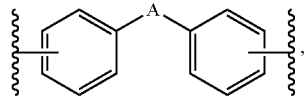

wherein A is S.

2. The polyphenylene polymer composition according to claim 1, wherein the polyphenylene polymer is polyphenylene sulfide.

3. The polyphenylene polymer composition according to claim 1, wherein n and m are each independently an integer selected from 8 to 25.

4. The polyphenylene polymer composition according to claim 1, wherein n and m are each independently an integer selected from 8 to 12.

5. The polyphenylene polymer composition according to claim 1, wherein the compound represented by formula 1 is N,N'-(4,4'-thiobis(4,1-phenylene))bis(decanamide) or N,N'-(4,4'-thiobis(4,1-phenylene))ditetradecanamide.

6. A compound which is N,N'-(4,4'-thiobis(4,1-phenylene))bis(decanamide).

7. A method for controlling the flowability of a polyphenylene polymer, comprising:
   adding a flowability controlling composition comprising a compound represented by formula 1 to the polyphenylene polymer at a concentration of 0.01-10 weight part to 100 weight part of the polyphenylene polymer; and
   melt mixing the flowability controlling composition and the polyphenylene polymer; wherein Formula 1 is

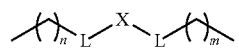

wherein
n and m are each independently an integer of 5 to 30;
L is C(=O)NH or NHC(=O); and
X is

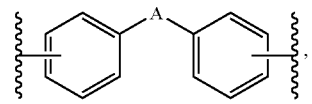

wherein A is S.

8. The method for controlling the flowability according to claim 7, wherein the polyphenylene polymer is polyphenylene sulfide.

* * * * *